(12) United States Patent
Walraevens et al.

(10) Patent No.: US 6,369,231 B1
(45) Date of Patent: Apr. 9, 2002

(54) PROCESS FOR PREPARATION OF 2-CHLOROPYRIDINE

(75) Inventors: René Walraevens; James Franklin; Paul Trouillet, all of Belgique (BE)

(73) Assignee: Reilly Industries, Inc., Indianapolis, IN (US)

(*) Notice: Subject to any disclaimer, the term of this patent is extended or adjusted under 35 U.S.C. 154(b) by 0 days.

(21) Appl. No.: 08/480,400

(22) Filed: Jun. 7, 1995

Related U.S. Application Data

(63) Continuation of application No. 07/857,101, filed on Mar. 25, 1992, now abandoned, which is a continuation of application No. 07/609,073, filed on Nov. 2, 1990, now abandoned, which is a continuation of application No. 07/370,170, filed on Jun. 20, 1989, now abandoned, which is a continuation of application No. 07/241,753, filed on Sep. 7, 1988, now abandoned, which is a continuation of application No. 06/894,354, filed on Aug. 7, 1986, now abandoned, which is a continuation of application No. 06/662,786, filed on Oct. 19, 1984, now abandoned.

(51) Int. Cl.$^7$ .................. C07D 211/72; C07C 17/00
(52) U.S. Cl. ..................... 546/345; 204/158
(58) Field of Search ............... 546/345; 204/158

(56) References Cited

U.S. PATENT DOCUMENTS

| | | | | |
|---|---|---|---|---|
| 2,284,479 A | * | 5/1942 | Rust et al. ............... | 260/654 |
| 2,299,441 A | * | 10/1942 | Vaughn et al. ........... | 260/662 |
| 2,324,248 A | * | 7/1943 | Vaughn et al. ........... | 260/662 |
| 2,324,249 A | * | 7/1943 | Vaughn et al. ........... | 260/662 |
| 2,820,791 A | * | 1/1958 | Shermer ............... | 546/345 X |
| 3,153,044 A | * | 10/1964 | Zaslowsky ............. | 546/345 |
| 3,173,919 A | * | 3/1965 | Johnston et al. ......... | 260/290 |
| 3,251,848 A | * | 5/1966 | Tarlin .................. | 260/290 |
| 3,297,556 A | * | 1/1967 | Boudakian et al. ....... | 204/158 |
| 3,370,062 A | * | 2/1968 | Corran ................. | 260/290 |
| 3,920,657 A | * | 11/1975 | Beschke et al. ......... | 260/290 HL |
| 3,929,907 A | * | 12/1975 | Janzon et al. ........... | 546/345 X |
| 3,969,205 A | * | 7/1976 | Kawamura et al. ....... | 204/158 |
| 4,054,499 A | * | 10/1977 | Kawamura et al. ....... | 204/158 |
| 4,257,857 A | * | 3/1981 | Whittaker et al. ........ | 204/158 |
| 4,284,783 A | * | 8/1981 | Whittaker et al. ........ | 546/345 |
| 4,288,600 A | * | 9/1981 | Roberts et al. .......... | 546/345 |
| 4,393,214 A | * | 7/1983 | Roberts et al. .......... | 546/345 |
| 4,752,644 A | * | 6/1988 | Jharvit et al. ........... | 546/345 |

FOREIGN PATENT DOCUMENTS

| | | | | |
|---|---|---|---|---|
| DE | 2252002 | * | 5/1974 | |
| DE | 3306905 | * | 8/1984 | ............... 546/345 |
| GB | 1461109 | * | 1/1977 | |

OTHER PUBLICATIONS

DeLa Mare et al, "Aromatic Substitutions Nitrations and Halogenation" pp. 194–197 (1959); Academic Press, New York, N.Y.*
Hertog, et al, *Rec Trav. Chim.*, 51, pp. 381–388 (1932).*
Wibaut, et al., *Rec. Trav. Chim.*, 58, pp. 709–721 (1939).*
Elderfield, *Heterocyclic Compounds*, vol. 1, pp. 504–509 (1950).*
Hertog, et al., *Rev. Trav. Chim.* 51, pp. 940–950 (1932).*
Vaughn, et al., *J. Org. Chem.* 5, pp. 449–471 (1940).*
Vaughn et al., *J. Org. Chem.*, 5, pp. 472–503 (1940).*
Mertel, "Pyridine and Its Derivatives", Part two, pp. 300–305 (1961); Interscience N.Y,N.Y.*
Abramovitch, "Pyridine and Its Derivatives," Supp. Part Two, pp. 407–411 (1974).*

* cited by examiner

*Primary Examiner*—Deborah C. Lambkin
(74) *Attorney, Agent, or Firm*—Woodard, Emhardt, Naughton, Moriarty & McNett

(57) ABSTRACT

Described are processes for producing 2-chloropyridine by reacting pyridine with molecular chlorine in the vapor phase in the presence of a catalyst which includes an organic compound which generates free radicals under the conditions of the reaction.

20 Claims, 1 Drawing Sheet

PROCESS FOR PREPARATION OF 2-CHLOROPYRIDINE

REFERENCE TO RELATED APPLICATIONS

This is a continuation of U.S. patent application Ser. No. 07/857,101 filed Mar. 25, 1992, abandoned, which is a continuation of U.S. patent application Ser. No. 07/609,073 filed Nov. 2, 1990, abandoned, which is a continuation of U.S. application Ser. No. 07/370,170 filed Jun. 20, 1989, abandoned, which is a continuation of U.S. patent application Ser. No. 07/241,753 filed Sep. 7, 1988, abandoned, which is a continuation of U.S. patent application Ser. No. 06/894,354 filed Aug. 7, 1986, abandoned, which is a continuation of U.S. application Ser. No. 06/662,786 filed Oct. 19, 1984, abandoned.

BACKGROUND

The present invention relates to a process for the preparation of 2-chloropyridine by chlorination of pyridine in the vapor phase in the presence of catalysts.

At this time, various techniques have been developed for the preparation of 2-halopyridines such as 2-chloropyridine. One of these techniques consists more particularly in the preparation of 2-chloropyridine by a chlorination reaction of pyridine by means of molecular chlorine. This technique was the subject of developments of processes that can be divided into two large classes.

A first class comprises the socalled thermal processes, conducted in the vapor phase at high temperature, generally above 250° C. and even 300 to 400° C., and described primarily in U.S. Pat. Nos. 2,820,791 and 3,153,044 in the name of OLIN MATHIESON. These processes have various drawbacks such as a substantial formation of tars, causing the reactors or the ducts to clog up, and hence makes continuous execution of the process difficult. Furthermore these processes are accompanied according to the inventors, by high risks of explosion as well as corrosion.

A second class of processes comprises the processes initiated by means of light or ultraviolet radiation. Such processes have been described in particular in U.S. Pat. No. 3,297,556 in the name of OLIN MATHIESON and U.S. Pat. No. 4,054,499 in the name of SEITETSU KAGAKI Co. These processes, although they can be operated at lower temperatures than the socalled thermal processes, have the drawbacks of leading to the formation of tarry sub products that contaminate the light tubes and give rise to a subsequent diminution in the yield of the reaction. Furthermore these processes have to be operated in reactors permeable to the initiating radiation, that is to say more generally made of glass, which means that reactions embodied at high pressure are impracticable.

SUMMARY OF THE INVENTION

It is the object of the present invention to provide a new class of procedure for making 2-chloropyridine, and in general the 2-halo-pyridines without the drawbacks of the processes in the two classes described above.

The invention relates to a process for the preparation of 2-chloropyridine by a reaction of chlorination of pyridine by means of molecular chlorine, conducted in the vapor phase and with the intervention of catalysts, in which the catalysts utilized include at least one organic compound capable of generating free radicals under the conditions of the chlorination reaction.

BRIEF DESCRIPTION OF THE FIGURE

The FIGURE provides a schematic illustration of a laboratory apparatus which can be used to carry out processes of the invention.

DESCRIPTION OF THE PREFERRED EMBODIMENT

Figure 1:
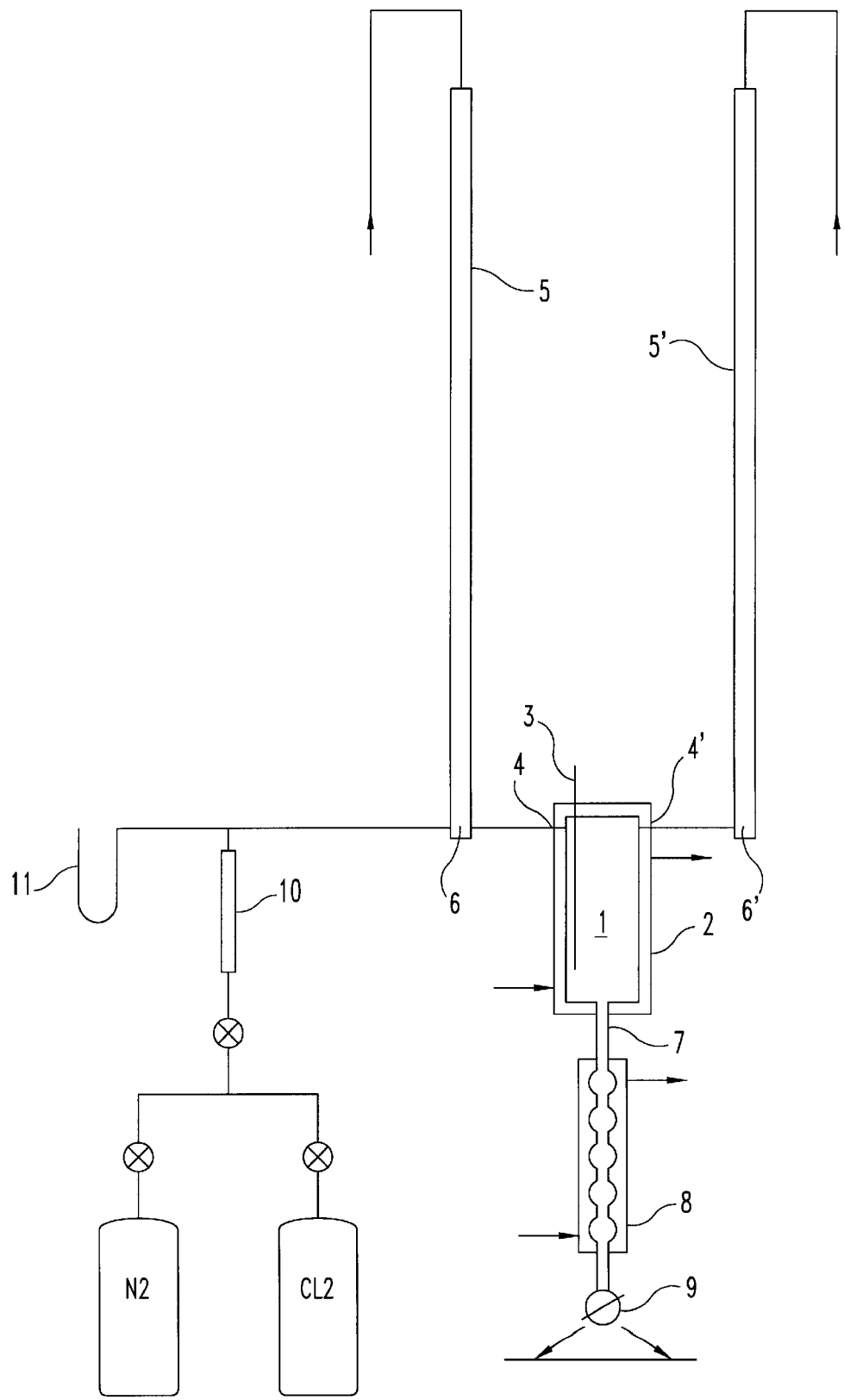

The term chlorination reaction conducted in the vapor phase as used by the Applicant stands for a chlorination reaction embodied under conditions of temperature and pressure such that all the reagents, additives, catalysts and products issuing from the reaction are in the vapor state in the reaction medium.

When operating at atmospheric pressure, these conditions are met for temperatures above 150° C. Good results have been obtained at temperatures lying between 175 and 275° C. and more particularly between 200 and 250° C.

The term organic compounds capable of generating free radicals under the conditions of the chlorination reaction stands for any compound capable of breaking down with formation of at least one organic radical at temperatures and pressures such that the chlorination reaction takes place in the vapor phase. Such organic compounds comprise not only the chemical products constituted solely by organic entities such as the organic peroxides or nitrogen derivatives such as the azoalkalines or nitriles of the azo-bis-isobutyronitrile type, but also chemical products comprising an inorganic part in the molecule such as the mixed organic-inorganic peroxides and the organo-metallic derivatives such as tetraethyl lead.

As a rule the chlorination reaction is catalyzed by peroxides or peroxide derivatives of organic type. Very suitable among these are the hydroperoxides, the alpha-oxy- and alpha-peroxy-hydroperoxides and—-peroxides, the peroxides, diacylperoxides, peroxyacids and peroxyesters such as in particular those defined in the Encyclopedia of Chemical Technology, Kirk-Othmer, Third Edition, Volume 17, pages 27 to 89, published by J. Wiley & Sons New York, 1982, are highly suitable. Among these peroxide products, good results have been obtained with the alkyl peresters of aliphatic or aromatic acids and with dialkyl peroxides. The best results were obtained with tertiary butyl perbenzoate, tertiary butyl per-2-ethylhexanoate, tertiary butyl perpivalate, tertiary amyl per-pivalate and di-tertiary butyl peroxide. And finally, among these, di-tertiary butyl peroxide gave the best results.

The quantity of organic compounds capable of generating free radicals which is utilized depends on the chemical nature of the organic compound involved. When working with peroxides such as di-tertiary butyl peroxide, 0.05 to 5 mol % of this peroxide is used, calculated on the basis of the pyridine involved; the preferred quantities lie between 0.1 and 2 mol % based on the pyridine involved.

The molecular chlorine and the pyridine are usually applied in molar ratios comprised between 0.1 to 10 moles of chlorine per mole of pyridine. It is preferable to utilize 0.2 to 2 moles of chlorine per mole of pyridine; and highest preference is given to molar ratios of chlorine to pyridine of between 0.3 and 1 mole of chlorine per mole of pyridine.

Aside from the reagents and catalysts cited above, it is possible with advantage to utilize, in the process according to the invention, additives such as water vapor, nitrogen and/or other gases which do not participate in the chlorination reaction properly speaking. As a rule the chlorination reaction is embodied in the presence of water vapor in the proportion of 0.1 to 25 moles per mole of pyridine utilized. It is preferable to use water vapor in quantities of 1 to 15 moles per mole of pyridine. The adjunction of these additives and more particularly of the water vapor, can be embodied in any manner at all. One advantageous manner consists in premixing the water and pyridine, sending this mixture into an evaporator, and then injecting the vapors thus obtained into the chlorination reactor properly speaking.

It has also been found desireable in order to insure a good homogenization of the reagents and catalysts, to conduct the chlorination reaction in the presence of additives of an organic nature which act as solvents or diluents but which are inert with respect to the reagents and catalysts intervening in the chlorination reaction. As organic additives it is common to use organic halogen compounds. Among these it is preferable to operate with chlorine derivatives of aliphatic compounds which can be used in conjunction with the water vapor in the reaction medium in order to minimize the overheating of the reagents and the reactor owing to the exothermicity of the chlorination reaction.

As chlorine derivatives suitable as organic additives it is possible to use products such as carbon tetrachloride or other halogen derivates which are inert under the conditions of chlorination. It is preferable to operate with carbon tetrachloride.

In general, the halogenated organic additives are added to the reaction medium in a proportion of 1 to 25 moles per mole of pyridine utilized. When carbon tetrachloride is used as organic additive, the preferred quantities lie between 1.5 and 10 moles per mole of pyridine utilized.

The process according to the invention can be embodied in any apparatus or any reactor that makes it possible to combine the operational conditions described above. Good results have been obtained in apparatus that permits the obtention of good homogenization of the reagents with the catalysts and the various additives, as well as an introduction of the reagents and catalysts at relatively high speeds.

A laboratory apparatus meeting these criteria is represented in the attached FIGURE. This apparatus comprises a cylindrical tube with a diameter of 112 mm and a height of 280 mm, forming a reaction chamber (1) and a jacket (2) which is heated by circulation of oil through jacket (2). The reaction chamber (2) is equipped with a sheath for thermocouples (3) with an outer diameter of 8 mm, for measuring the temperature at different points. The top of the reaction chamber is equipped with two horizontal inputs, 6 mm in diameter (4) and (4') placed at 90° to one another and used for the tangential injection of the vaporized reagents. The gaseous products are allowed to leave the reaction chamber at the bottom through tube (7) with a diameter of 20 mm.

The liquid reagents, additives and catalysts comprising, on the one hand a solution of organic peroxide in carbon tetrachloride and on the other hand, pyridine and water, are fed respectively at the head of two vertical, stainless steel tubes (5) and (5') with a height of 1.5 m and an inner diameter of 15 mm, in which they are vaporized by electric heating. The temperature of the vapors is then measured, respectively, by means of thermocouples (6) and (6') mounted in the foot of each stainless steel tube close to the inputs (4) and (4') of the reaction chamber to which the stainless steel tubes (5) and (5') are connected by means of TEFLON unions.

The molecular chlorine gas, perhaps supplemented by nitrogen, whose flow is measured by a rotameter (10) and a mercury manometer (11), is injected as is into the foot of tube (5), in which the carbon tetrachloride is vaporized.

The gaseous reaction products issuing from the reaction are eliminated through tube (7) and then condensed in a pyrex condenser (8) 300 mm long equipped with a water-cooling jacket and a 2-way valve (9) of pyrex.

The condensed products collected by valve (9) can undergo various treatments and can, for example, be purified.

One manner of operating consists in violently agitating the products of condensation with a sufficient quantity of a basic reagent such as NaOH to neutralize all of the molecular chlorine and hydrochloric acid remaining. After decantation of the liquid, two phases are formed, constituted on the one hand by a heavy organic phase comprising carbon tetrachloride, a part of the residual pyridine as well as the products of chlorination such as 2-chloropyridine and the major part of the products or ions of non-organic nature. The phases are separated and the pyridine from the aqueous phase is recovered by extraction with a solvent, generally a halogen, such as carbon tetrachloride and preferably chloroform. The various organic phases are then combined and the 2-chloropyridine can be separated from this medium by an operation of rectification.

The 2-chloropyridine obtained according to the process of the invention can be used in all known applications of this product, that is to say, as chemical intermediary for the manufacture, in particular of products for agriculture, cosmetics and pharmaceutical products.

The reaction of chlorination of the pyridine can, of course, by means of obvious technical implementations proper to the various products concerned, be applied to other aromatic heterocyclic compounds.

The examples which follow serve to illustrate the invention without, however, limiting its scope.

EXAMPLE 1

In an apparatus such as the one illustrated in the FIGURE and having the characteristics described above, we continuously introduce through tube (5), kept at 144° C., 8.2 moles of carbon tetrachloride mixed with 0.041 mole of di-tertiary butyl peroxide per hour, and through tube (5'), kept at 140° C., 3.27 moles of pyridine and 3.50 moles of water per hour. In addition, we continuously inject at the foot of tube (5), 2.18 moles of molecular chlorine gas per hour. The evaporated reagents, catalyst and additives are then continuously introduced through inputs (4) and (4') respectively into reaction chamber (1) heated to about 240° C. by means of oil circulating in the jacket (2). After 1 hour of coming up to schedule the readings are 242° C. at the top 244° C. in the middle and 241° C. at the bottom of the reaction chamber and then there is a continuous collection, hourly, through channel 9 of a mixture of liquid having the following composition:

2-chloropyridine: 1.136 mole 3-chloropyridine: 0.006 mole 4-chloropyridine: 0.004 mole 2.6-dichloropyridine: 0.234 mole other dichloropyridines: 0.002 mole pyridine: 2.089 moles The time of stay of the reagents in the reactor is 13 seconds, and the 2-chloropyridine yield of the reaction is 35% per mole calculated on the basis of the pyridine utilized; the selectivity of the chlorine products issuing from the chlorination is 96% where 2-chloropyridine is concerned.

EXAMPLES 2, 3 AND 4

We operate as in example 1 but with quantities of reagents, additives and catalyst, and temperatures as shown in the table below. The results observed are likewise shown in the table.

| Parameters | Example 2 | Example 3 | Example 4 |
|---|---|---|---|
| Feed at mole/hour | | | |
| (5) carbon tetrachloride | 4.05 | 4.04 | 4.05 |
| (5) di-tertiary butyi peroxide | 0.0204 | 0.0102 | 0.005 |
| (5') pyridine | 1.59 | 1.59 | 1.60 |
| (5') water | 1.71 | 1.74 | 1.66 |
| foot of tube (5) chlorine | 1.09 | 1.09 | 1.09 |
| Temperatures ° C. | | | |
| tube (5) | 151 | 151 | 135 |
| tube (5') | 166 | 151 | 144 |
| reaction chamber (1) | | | |
| top | 232 | 232 | 231 |
| middle | 232 | 233 | 234 |
| bottom | 231 | 231 | 233 |
| Time of stay of reagents in seconds | 26 | 26 | 26 |
| Products collected through channel (9) mole/hour | | | |
| 2-chloropyridine | 0.594 | 0.607 | 0.574 |
| 3-chloropyridine | 0.003 | 0.003 | 0.003 |
| 4-chloropyridine | 0.002 | 0.002 | 0.002 |
| 2,6-dischoropyridine | 0.017 | 0.019 | 0.016 |
| other dichloropyridines | 0.001 | 0.001 | 0.001 |
| pyridine | 0.974 | 0.959 | 1.005 |

The yields of 2-chloropyridine obtained are, respectively, 37% (example 2), 38% (example 3) and 36% (example 4) per mole calculated on the basis of the pyridine. The respective selectivities are 96% (example 2), 96% (example 3) and 96% (example 4).

Comparison of the results of examples 1 to 4 reveals that the reaction of chlorination of pyridine to 2-chloropyridine is catalyzed even by small amounts of peroxides and is very little affected by fluations of 100 to 200% of this FIGURE.

What is claimed is:

1. A process for selectively preparing 2-chloropyridine, comprising:
    (a) providing a vapor reaction chamber equipped for continuous passage of vapors through the reaction chamber;
    (b) heating the reaction chamber at a temperature of about 175° C. to about 275° C., to provide a heated reaction chamber;
    (c) continuously passing vaporized pyridine into the heated reaction chamber;
    (d) continuously passing vaporized molecular chlorine into the heated reaction chamber along with the pyridine, wherein the molecular chlorine is passed into the heated reaction chamber in a molar ratio of about 0.1 to 10 relative to the pyridine;
    (e) continuously passing a vaporized catalyst into the heated reaction chamber along with the pyridine and molecular chlorine, the catalyst including an organic peroxide compound which generates free radicals in the heated reaction chamber;
    (f) continuously passing vaporized water into the heated reaction chamber along with the vaporized pyridine, molecular chlorine and catalyst, wherein the vaporized water is passed into the heated reaction chamber in a molar ratio of about 0.1 to about 25 relative to the pyridine.
    (g) continuously passing a vaporized halogenated organic diluent into the heated reaction chamber along with the vaporized pyridine, molecular chlorine, catalyst and water, wherein the diluent is passed into the heated reaction chamber in a molar ration of about 1 to about 25 relative to the pyridine; and
    (h) continuously collecting from the reaction chamber a reacted mixture produced by steps (a)–(g) and containing the 2-chloropyridine, and wherein said 2-chloropyridine is prepared at a selectivity of above 90%.

2. The process of claim 1, wherein the vaporized pyridine and vaporized water are combined and then passed together into the heated reaction chamber, and the vaporized molecular chlorine, vaporized catalyst, and vaporized halogenated organic diluent are combined and then passed together into the heated reaction chamber.

3. The process of claim 2, wherein the organic peroxide is a dialkyl peroxide, an alkyl ester of an aliphatic acid, or an alkyl ester of an aromatic acid.

4. The process of claim 3, wherein the organic peroxide is selected from the group consisting of tertiary butyl perbenzoate, tertiary butyl per-2-ethylhexanoate, tertiary butyl perpivalate, tertiary amyl per-pivalate and di-tertiary butyl peroxide.

5. The process of claim 4, wherein the organic peroxide is di-tertiary butyl peroxide.

6. The process of claim 1, wherein:
    the molecular chlorine is passed into the heated reaction chamber in a molar ratio of about 0.2 to 2 moles relative to the pyridine; and
    the vaporized water is passed into the heated reaction chamber in a molar ratio of about 1 to about 15 relative to the pyridine.

7. The process of claim 2, wherein:
    the molecular chlorine is passed into the heated reaction chamber in a molar ratio of about 0.2 to 2 moles relative to the pyridine; and
    the vaporized water is passed into the heated reaction chamber in a molar ratio of about 1 to about 15 relative to the pyridine.

8. The process of claim 7, wherein:
    the molecular chlorine is passed into the heated reaction chamber in a molar ratio of about 0.3 to 1 relative to the pyridine.

9. A process for selectively preparing 2-chloropyridine comprising reacting pyridine with molecular chlorine in the vapor phase in the presence of a catalyst at a temperature of about 175° C. to about 275° C., the catalyst including at least one organic peroxide compound which generates free radicals under the conditions of said reacting, so as to prepare 2-chloropyridine at a selectivity above about 95%.

10. A process for selectively preparing 2-chloropyridine comprising reacting pyridine with molecular chlorine in vapor phase in the presence of an organic peroxide compound which generates free radicals under the conditions of said reacting, said organic peroxide compound being present during said reacting in an amount of about 0.05 mole % to about 5 mole % based on said pyridine, and said reacting conducted at a temperature of about 175° C. to about 275° C., so as to selectively produce 2-chloropyridine.

11. The process of claim 10, wherein the vaporized pyridine and vaporized water are combined and then passed together into the heated reaction chamber, and the vaporized molecular chlorine, vaporized catalyst, and vaporized halogenated organic diluent are combined and then passed together into the heated reaction chamber.

12. The process of claim 11 wherein the organic peroxide compound is a dialkyl peroxide, an alkyl ester of an aliphatic acid, or an alkyl ester of an aromatic acid.

13. The process of claim 12 wherein the organic peroxide compound is selected from the group consisting of tertiary butyl perbenzoate, tertiary butyl per-2-ethylhexanoate, tertiary butyl perpivalate, tertiary amyl per-pivalate and di-tertiary butyl peroxide.

14. The process of claim 13 wherein the organic peroxide compound is di-tertiary butyl peroxide.

15. The process of claim 10, which comprises:
(a) providing a vapor reaction chamber equipped for continuous passage of vapors through the reaction chamber;
(b) heating the reaction chamber at a temperature of about 175° C. to about 275° C., to provide a heated reaction chamber;
(c) continuously passing vaporized pyridine into the heated reaction chamber;
(d) continuously passing vaporized molecular chlorine into the heated reaction chamber along with the pyridine, wherein the molecular chlorine is passed into the heated reaction chamber in a molar ratio of about 0.1 to about 10 relative to the pyridine;
(e) continuously passing vaporized catalyst into the heated reaction chamber along with the pyridine and molecular chlorine, the catalyst including an organic compound which generates free radicals in the heated reaction chamber and being passed into the heated reaction chamber in an amount of about 0.05 mole % to about 5mole % relative to the pyridine;
(f) continuously passing vaporized water into the heated reaction chamber along with the vaporized pyridine, molecular chlorine, and catalyst, wherein the vaporized water is passed into the heated reaction chamber in a molar ratio of about 0.1 to about 25 relative to the pyridine;
(g) continuously passing a vaporized halogenated organic diluent into the heated reaction chamber along with the vaporized pyridine, molecular chlorine, catalyst and water, wherein the diluent is passed into the heated reaction chamber in a molar ratio of about 1 to about 25 relative to the pyridine; and
(h) continuously collecting from the reaction chamber a reacted mixture produced by steps (a)–(g) and containing the 2-chloropyridine.

16. The process of claim 15, wherein said organic compound is an organic peroxide compound.

17. A process for selectively preparing 2-chloropyridine, comprising:
(a) providing a vapor reaction chamber equipped for continuous passage of vapors through the reaction chamber;
(b) heating the reaction chamber at a temperature of about 175° C. to about 275° C., to provide a heated reaction chamber;
(c) continuously passing vaporized pyridine into the heated reaction chamber;
(d) continuously passing vaporized molecular chlorine into the heated reaction chamber along with the pyridine, wherein the molecular chlorine is passed into the heated reaction chamber in a molar ratio of about 0.1 to about 10 relative to the pyridine;
(e) continuously passing a vaporized organic peroxide compound into the heated reaction chamber along with the pyridine and molecular chlorine, the organic peroxide compound generating free radicals in the heated reaction chamber and being passed into the heated reaction chamber in an amount of about 0.05 mole % to about 5 mole % relative to the pyridine;
(f) continuously passing vaporized water into the heated reaction chamber along with the vaporized pyridine, molecular chlorine, and catalyst, wherein the vaporized water is passed into the heated reaction chamber in a molar ratio of about 0.1 to about 25 relative to the pyridine;
(g) continuously passing a vaporized halogenated organic diluent into the heated reaction chamber along with the vaporized pyridine, molecular chlorine, catalyst and water, wherein the diluent is passed into the heated reaction chamber in a molar ratio of about 1 to about 25 relative to the pyridine; and
(h) continuously collecting from the reaction chamber a reacted mixture produced by steps (a)–(g) and containing the 2-chloropyridine.

18. The process of claim 15 wherein the organic peroxide compound is a dialkyl peroxide, an alkyl ester of an aliphatic acid, or an alkyl ester of an aromatic acid.

19. The process of claim 18 wherein the organic peroxide compound is selected from the group consisting of tertiary butyl perbenzoate, tertiary butyl per-2-ethylhexanoate, tertiary butyl per-pipalate, tertiary amyl per-pipalate and di-tertiary butyl peroxide.

20. The process of claim 19 wherein the organic peroxide compound is di-tertiary butyl peroxide.

* * * * *